(12) United States Patent
Grove et al.

(10) Patent No.: US 7,219,998 B2
(45) Date of Patent: May 22, 2007

(54) DOT RADIAL RINGED PLACIDO

(75) Inventors: Donald Charles Grove, Layton, UT (US); Lloyd G. Allred, Bountiful, UT (US)

(73) Assignee: Bausch and Lomb Incorporated, Rochester, NY (US)

( * ) Notice: Subject to any disclaimer, the term of this patent is extended or adjusted under 35 U.S.C. 154(b) by 132 days.

(21) Appl. No.: 11/013,597

(22) Filed: Dec. 16, 2004

(65) Prior Publication Data

US 2006/0132712 A1    Jun. 22, 2006

(51) Int. Cl.
*A61B 3/10* (2006.01)
(52) U.S. Cl. .................................... 351/212
(58) Field of Classification Search ........ 351/205–212, 351/239; 356/2; 606/4, 5
See application file for complete search history.

(56) References Cited

U.S. PATENT DOCUMENTS

| | | | |
|---|---|---|---|
| 3,804,528 A | 4/1974 | Kilmer et al. | 356/165 |
| 5,054,907 A * | 10/1991 | Sklar et al. | 351/212 |
| 5,864,383 A | 1/1999 | Turner et al. | 351/212 |
| 6,059,773 A | 5/2000 | Maloney et al. | |
| 6,213,605 B1 | 4/2001 | D'Souza et al. | 351/212 |
| 6,447,119 B1 * | 9/2002 | Stewart et al. | 351/212 |
| 6,834,959 B2 | 12/2004 | Niven et al. | 351/212 |
| 2004/0061833 A1 | 4/2004 | Niven et al. | |

FOREIGN PATENT DOCUMENTS

WO    WO 99/34725 A    7/1999

OTHER PUBLICATIONS

International Search Report (PCT/ISA/220) and Written Opinion (PCA/ISA/237) mailed on Apr. 19, 2006.

* cited by examiner

*Primary Examiner*—Hung Xuan Dang
*Assistant Examiner*—Joseph Martinez

(57) ABSTRACT

An ophthalmic placido pattern 10 is used to determine a curvature of an anterior surface of a cornea of an eye. The pattern 10 includes a series of alternating light and dark concentric rings 12 and 14 centered about a central point 16. A series of shaped geometric shapes 18 and 20 are placed about at least some of the concentric rings 12 and 14. The shapes 18 and 20 are of a contrasting color with respect to the ring 12 or 14 on which the shape 18 or 20 is placed.

5 Claims, 7 Drawing Sheets

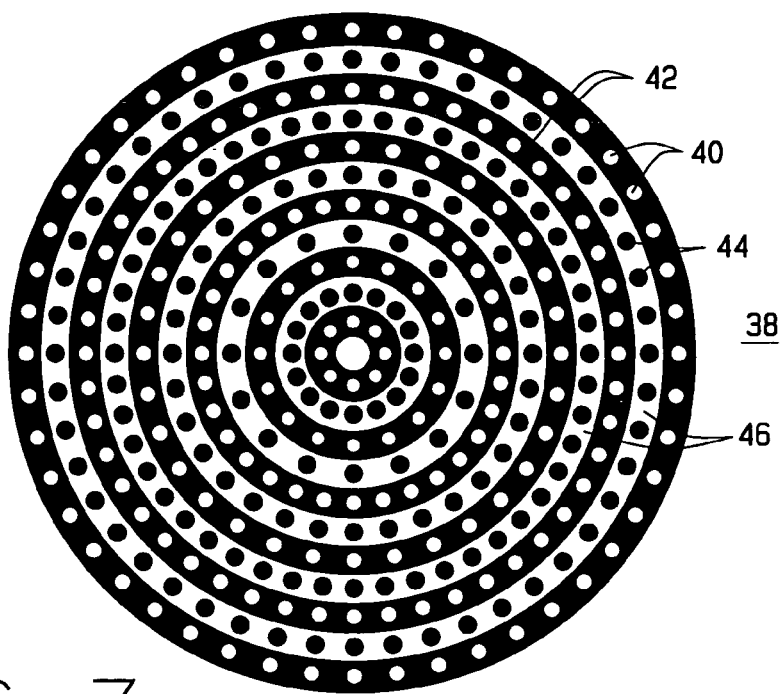
FIG. 7
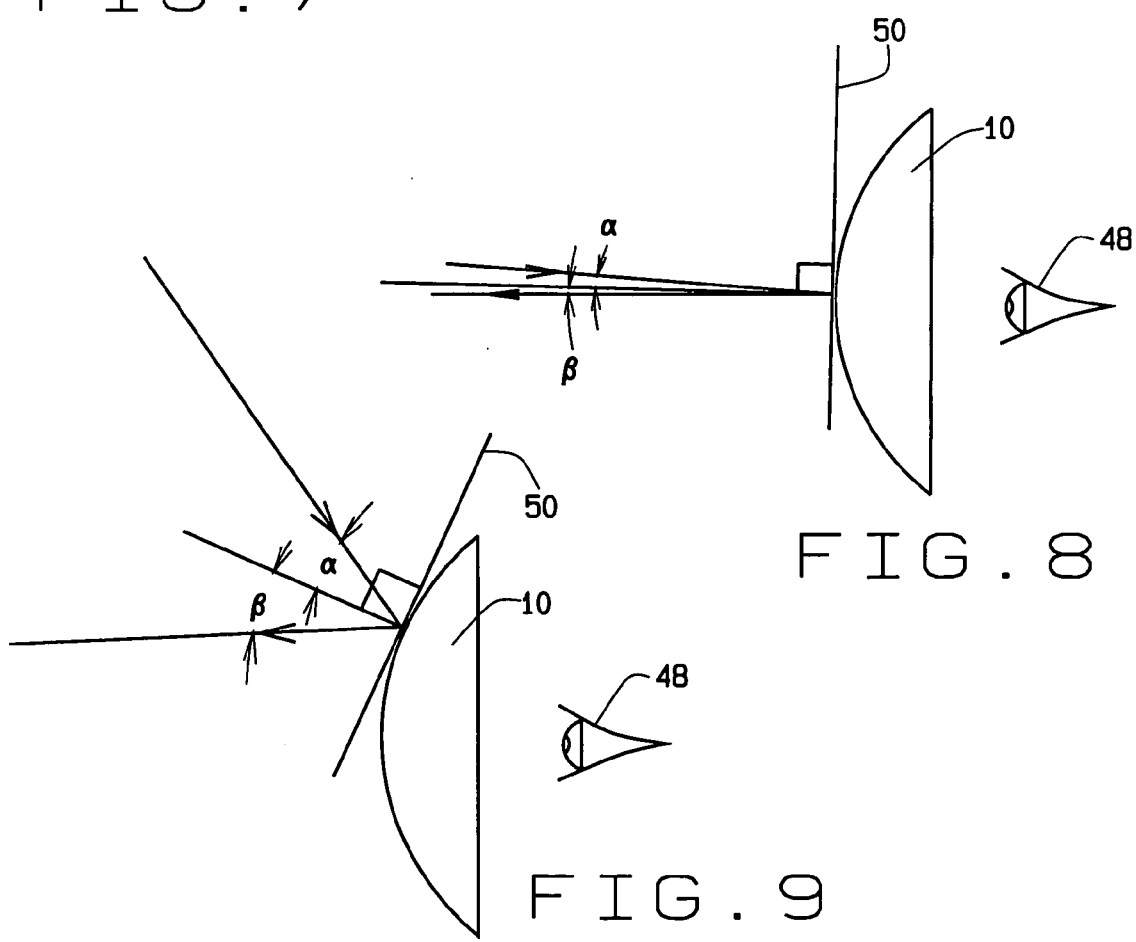
FIG. 8
FIG. 9

DOT RADIAL RINGED PLACIDO

BACKGROUND OF THE INVENTION

1. Field of the Invention

The present invention relates to a novel placido pattern. More specifically, the novel placido pattern of the present invention allows for easier, more accurate, and more economical detection of concentric anomalies that may occur on the eye being examined.

2. Description of Related Art

Placido imaging and placido examinations commonly referred to as keratometry date back over 150 years. Traditionally keratometry enables measurements of eye curvature that depend on the fixturings used, as well as set-up geometry. Using keratometry, the geometry of an eye can be derived manually by examination of a photograph. A reference placido pattern is first captured photographically after being reflected off of a sphere of known radius. A fundamental theorem of placido geometry states that the magnification of the reflected placido image is directly proportional to the radius of curvature of the examined object. Traditional patterns typically employed a series of concentric light and dark circles, such as shown in FIG. 1.

The concentric ring pattern of FIG. 1 developed by Placido was developed on the premise that the concentric ring patterns reflected from the human cornea would distort based on the anterior shape of the examined cornea. In the case of radical change of curvature of the cornea, such as a smaller radius or more curvature, the rings would appear to be further apart. For areas that are larger in radius, the rings would appear to be closer together. For a perfectly spherical cornea, the rings remain concentric and evenly spaced.

Within the last twenty years or so, it has been found that if a recording device, such as a camera, captures these images, the captured images can be compared to an image from the reflection of a close-to-perfect reference sphere. The differences between the two images then indicate how much the curvature of the anterior surface of the examined eye has changed from a perfect sphere. Other prior art placido patterns include a spider-web pattern, which is fully described in U.S. Publication 2004-0061833 and is commonly assigned with the present invention to Bausch & Lomb Incorporated. An example of such spider-web pattern is shown in FIG. 2. FIG. 3 shows yet another prior art placido patter which may be referred to as a dartboard pattern. The dartboard pattern can be said to be a combination of concentric and radial edges.

A camera typically is placed behind a hole in the center of the placido pattern and is aimed toward a patient's eye. During an acquisition of an image of the eye with a reflected placido pattern, the device is placed in an appropriate location in front of the eye. The surface of the cornea of the eye being examined then reflects the pattern and the images captured by the camera placed behind the placido pattern. The reflection of the pattern will change or distort depending on the changes in curvature on the corneal surface from that of a perfect sphere. With certain image processes and analysis software in known instruments, such as the Bausch & Lomb Incorporated Orbscan II™ Systems or other known keratometers or topography systems, it is possible to build a curvature map of the anterior surface of the cornea being examined.

A major problem with the ringed placido of FIG. 1, is the possibility of acquiring ambiguous data. If a curvature anomaly occurs, tangentially to a ringed edge from the X-Y perspective of the eye image, an ambiguity may occur. This is referred to as a concentric anomaly. Another type of anomaly that may be found is a radial anomaly. A radial anomaly is detected from the reflection of the placido rings.

However, if specific points are added to the ring pattern in the middle of the rings, it is much easier to detect a concentric anomaly. The spider-web placido pattern of FIG. 2, does not share the limitation on detecting concentric anomalies with the pattern of FIG. 1. However, the algorithm required to find the edges in a spider-web placido pattern is very complex relative to the algorithms used for a simple placido pattern of FIG. 1. This is especially true since the concentric edges in the spider-web pattern are interrupted by radial lines or edges, which corrupt some of the relevant data with regard to the concentric edges.

The dartboard placido of FIG. 3 also does not have the concentric anomaly limitation of the simple ring placido. However, like the spider-web placido pattern, a more complex edge detection algorithm is required. In addition, the alternating black and white blocks do not produce smooth single edges, especially if the placido is slightly out of focus.

Therefore, it would be advantageous to have a placido pattern which can detect concentric anomalies relatively easily with the use of less complex edge detection algorithms required of some prior art patterns.

BRIEF DESCRIPTION OF DRAWINGS

FIG. 7 is yet another placido pattern in accordance with the present invention;

FIG. 8 is a depiction of incoming rays from near the center of a placido pattern;

FIG. 9 is an incoming ray from a wider angle then shown in FIG. 8;

DETAILED DESCRIPTION OF THE PREFERRED EMBODIMENT

Figure 4:
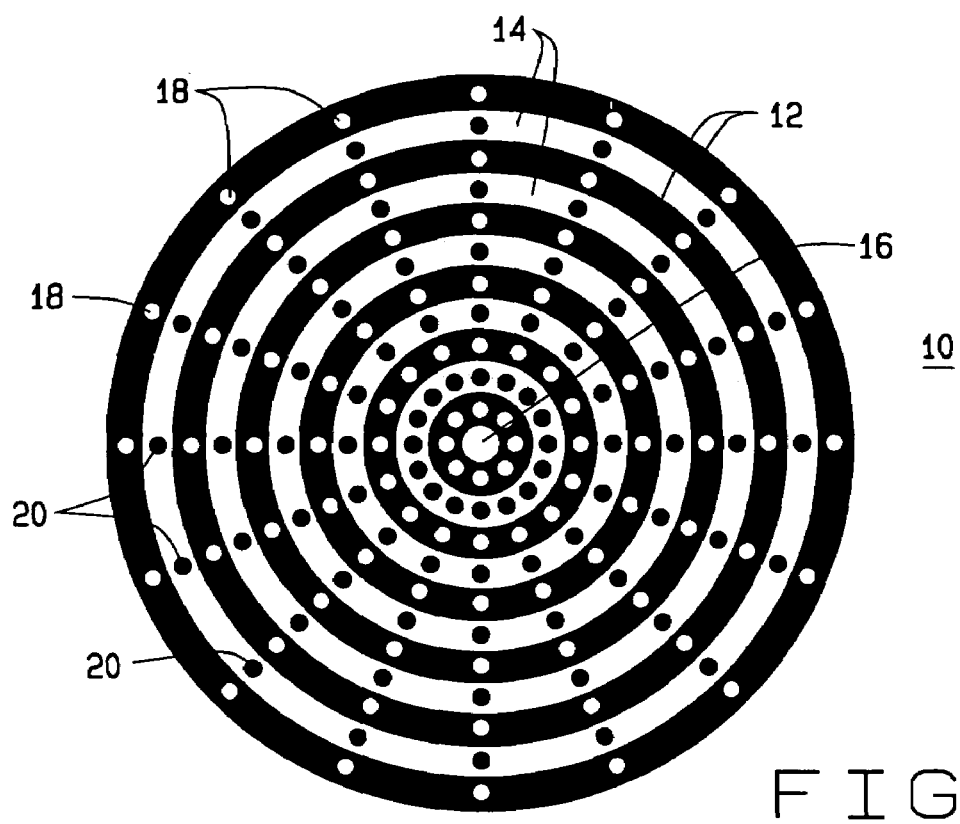
FIG. 4 is a placido pattern in accordance with the present invention.

FIG. 4 shows an ophthalmic placido pattern 10 for use in determining curvature of an anterior surface of a cornea of an eye, in accordance with the present invention. The pattern 10 includes a series of alternating light and dark concentric rings 12 and 14 centered about a central point 16. A series of spaced geometric shapes 18 and 20 are placed about at least some of the concentric rings 12 and 14. The geometric shapes 18 and 20 are of a contrasting color with respect to the ring 12 or 14 on which the geometric shape is placed. Preferably, the colors are black and white for the highest contrast though other colors may be used effectively.

The geometric shapes 18 and 20 are preferably circular dots, such as shown in FIG. 4, though other geometric shapes may be used as those skilled in the art will appreciate. The geometric shapes 18 are light colored relative to the rings 12 onto which they are placed. Likewise, the geometric shapes 20 are dark colored relative to the rings 14 onto which they are placed. Preferably the geometric shapes 18 and 20 are placed about every ring 12 and 14.

Figure 5:
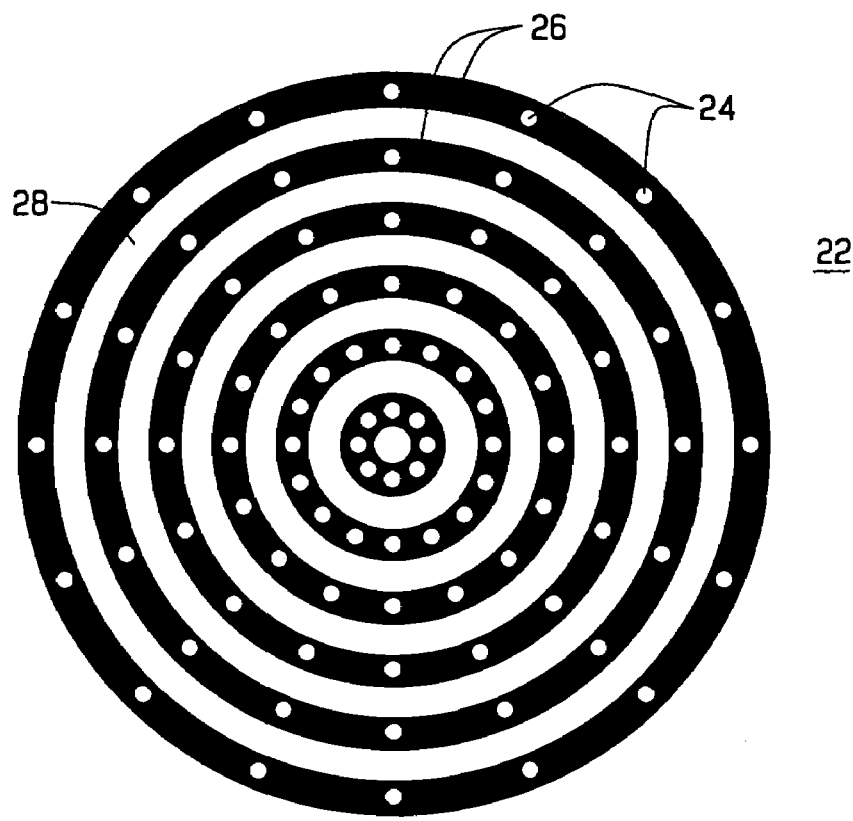
FIG. 5 is an alternate embodiment of a placido pattern in accordance with the present invention.

However as shown in FIG. 5, an alternate embodiment in accordance with the present invention, a placido pattern 22 may contain geometric shapes 24 only on every other ring. In the case of FIG. 5, the geometric shapes are light colored and placed about the dark colored rings 26. Whereas, the light colored rings 28 are devoid of any geometric shapes.

Figure 6:
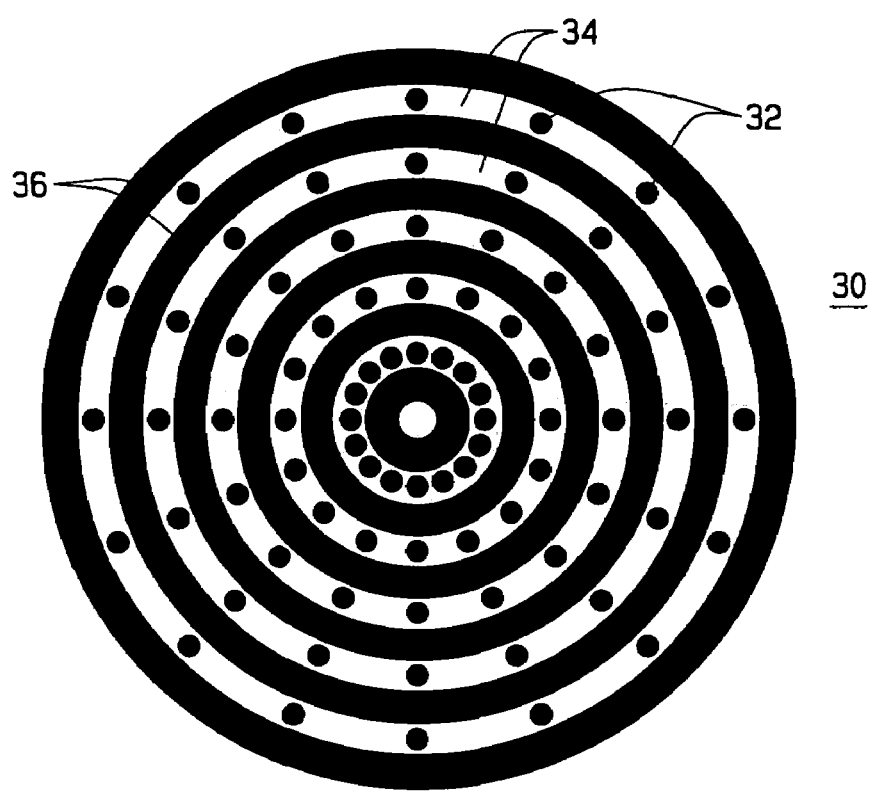
FIG. 6 is yet another alternate embodiment of a placido pattern in accordance with the present invention.
Figure 10:
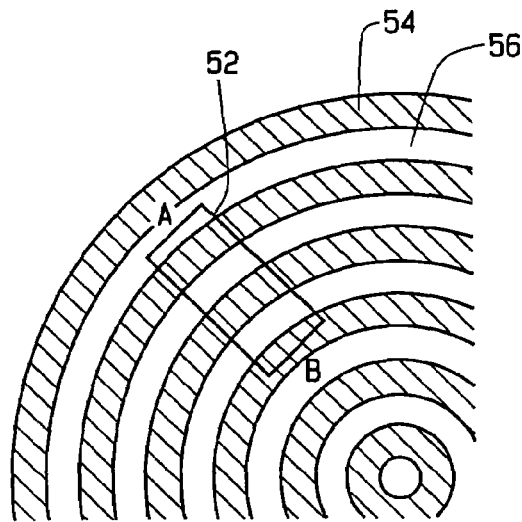
FIG. 10 is a partial view of a placido pattern including a reference surface section.
Figure 12:
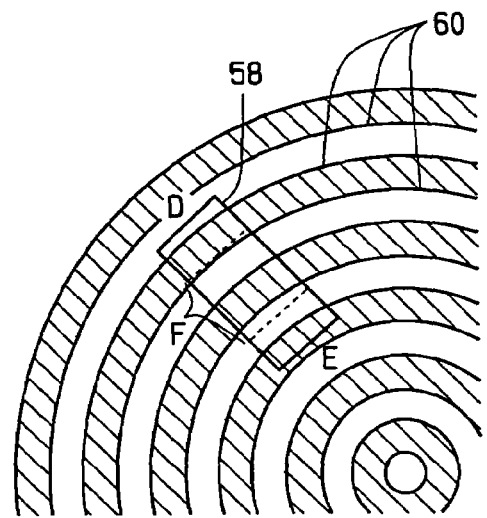
FIG. 12 is a partial placido pattern showing a surface segment to be measured.

FIG. 6 shows another alternate embodiment of a placido pattern 30, in accordance with the present invention. The placido pattern 30 of FIG. 6 is essentially the opposite of that shown in FIG. 5. That is dark geometric shapes 32 are placed about light colored rings 34 and the dark colored rings 36 are devoid of any geometric shapes.

FIG. 7 shows yet another alternate embodiment in accordance with the present invention of a placido pattern 38. The placido pattern 38 has light colored geometric shapes 40 on each dark colored ring 42 and dark colored geometric shapes 44 on each light colored ring 46. The difference between FIG. 7 and FIG. 4, is that the geometric shapes 40 and 44 are much more densely placed about the rings relative to FIG. 4.

The number of geometric shapes placed about the ring, depends on the amount of curvature data that is desired to be analyzed and which the algorithm of the system can handle. One potential drawback of FIG. 7 is that the geometric shapes 40 and 44 are too densely populated about the pattern 38 and therefore, the system may become confused as to which dot is being reflected by a patient's cornea if a severe but very small area of aberration occurs on the cornea being examined. Likewise, the patterns 22 and 30 may have insufficient geometric shapes placed on the patterns to reliably catch most of the concentric anomalies on a patient's eye. As those skilled in the art will appreciate, FIG. 4 most likely provides the best combination of a sufficient number of geometric shapes placed about the pattern without overly crowding the pattern with geometric shapes.

The dot radial ring placido patterns of FIGS. 4–7 are designed to track both radial and concentric anomalies on the surface of a cornea being examined. Typically as with a prior art ring placido, an eye is situated in front of an illuminated placido and camera. The camera and a computer capture the reflected image from the cornea. FIGS. 8 and 9 illustrate how light rays from the placido are reflected.

FIG. 8 shows incoming rays alpha and beta ($\alpha$ and $\beta$, respectively) that originate very near the center of the placido 10. The angle of reflection off of eye 48 depends on intersection position of a surface tangent plane 50 at a contact point of the incoming ray. The angles alpha and beta will be identical with respect to a surface normal from plane 50. Hence the angle of incidence equals the angle of reflection.

FIG. 9 shows the same phenomena, as that shown in FIG. 8, with the exception of an incoming ray from a wider angle. Despite the wider angle, the same rules hold true for both FIGS. 8 and 9.

Figure 11:
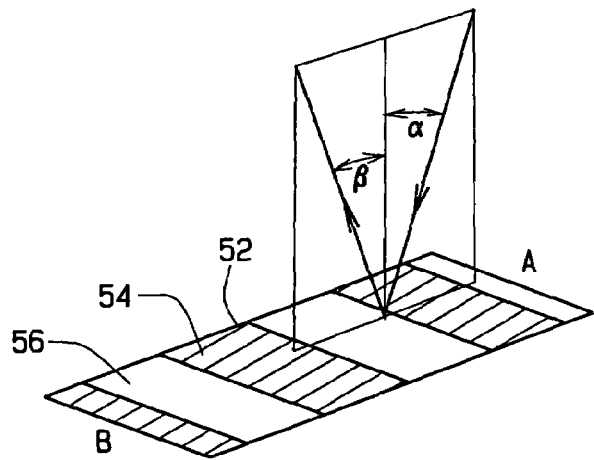
FIG. 11 depicts the surface segment of FIG. 10 along with its reflected image.

FIGS. 10–13 illustrate how a radial anomaly will affect the reflected image off the eye. The rectangle surface segment 52 with poles A and B moves across the rings 54 and 56. FIG. 11 shows the surface segment 52 below the reflected image. Note that for simplicity, all surface segments in all remaining FIGS. have been flattened and straightened as needed for two-dimensional view, but will still illustrate the concepts correctly. As those skilled in the art will appreciate, in actuality, the surface segments are a three-dimensional image taken from the concave shape of a typical placido pattern and reflection off of a cornea. As shown in FIG. 11, surface segment 52 has no anomalies across rings 54 and 56. Therefore, angles alpha and beta are equal with respect to the surface normal of the surface tangent plane.

Figure 13:
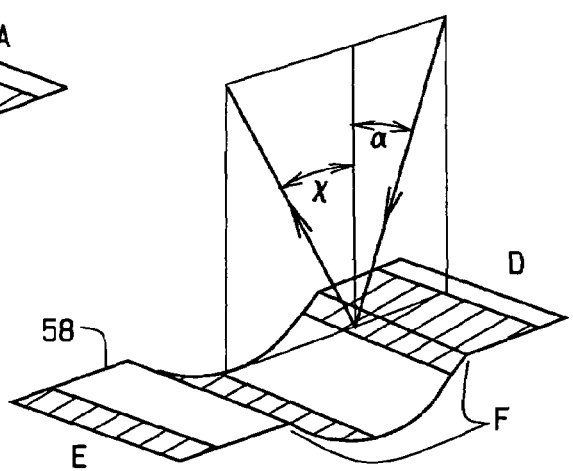
FIG. 13 shows the surface segment of FIG. 12 disclosing a radial anomaly.

Surface segment 58 with poles D and E shows a radial anomaly, that is, an anomaly that travels normal to or against ring edges 60. The effect of such a radial anomaly manifests itself as a warp or distortion in the ring edges 60. Note that the distorted ring edges 60 and surface segment 58 on the placido reflection of FIG. 12 within the bounds of the dashed-lines are marked as F. FIG. 13 shows the segment 58 below the reflection and illustrates what would occur with the radial anomaly contained within surface segment 58. An incoming ray defined by angle alpha contacts the surface at a different angle than that of FIG. 11. This affects the surface normal at the point of contact. Hence, the angle of reflection has changed from beta, which is equal to alpha to a new angle X. The change in reflected angle results in a distorted reflection when using the same surface normal tangent plane as that in FIG. 11. However, it is noted that rings 54 and 56 outside the distortion bounds F are not distorted on the reflection.

Figure 14:
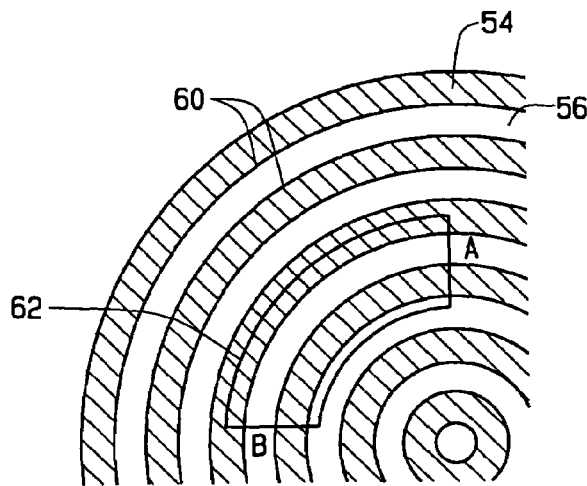
FIG. 14 is a partial view of placido pattern including a surface segment.
Figure 16:
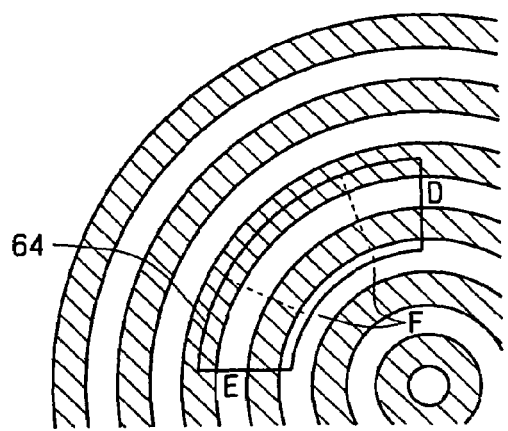
FIG. 16 is a partial view of a placido pattern along with a surface segment.
Figure 15:
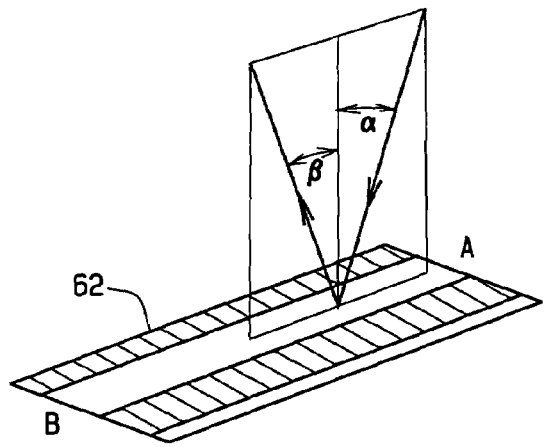
FIG. 15 depicts the surface segment of FIG. 14 along with the reflected image.
Figure 17:
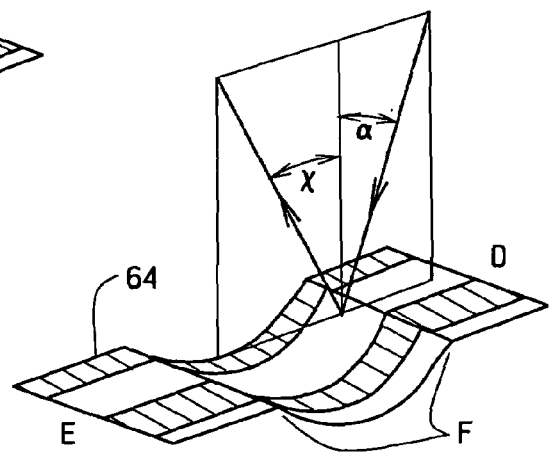
FIG. 17 depicts the surface segment of FIG. 16 and illustrates a concentric anomaly.

FIGS. 14–17 illustrates a concentric anomaly. A concentric anomaly moves tangently or with the ring edges 60. In FIG. 14, the surface segment 62 with poles A and B are formed with the rings or tangent to the rings. A problem with detecting a concentric anomaly occurs when the distortion occurs in surface segment 64 with poles D and E of FIG. 16. FIG. 15 shows surface segment 62 wherein the reflected image or ray beta is equal to the incoming ray alpha and has no distortion. However, FIG. 17 shows that surface segment 64 is being distorted just as the radial anomaly of FIG. 13 is distorted. However, the distortion of FIG. 17 is hidden due to the fact that the same color surfaces are being viewed within the concentric anomaly. Since there is no other frame of reference, a concentric anomaly on a ring placido can be hidden or at the very least, significantly attenuated. So while the image still is being distorted, an operator or the camera taking the photograph cannot detect this error because it is running with the rings 54 and 56.

Figure 1:
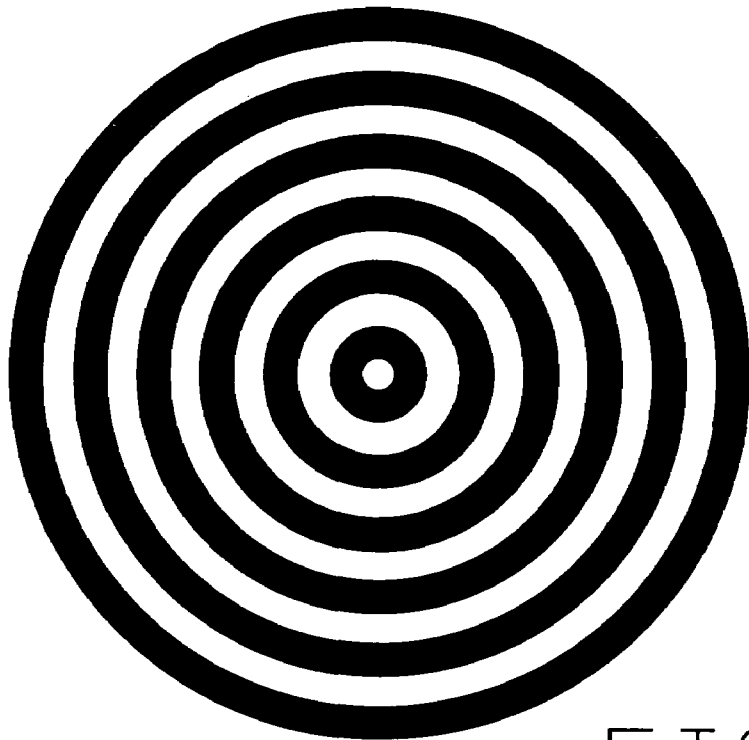
FIG. 1 is a depiction of a prior art placido pattern.
Figure 2:
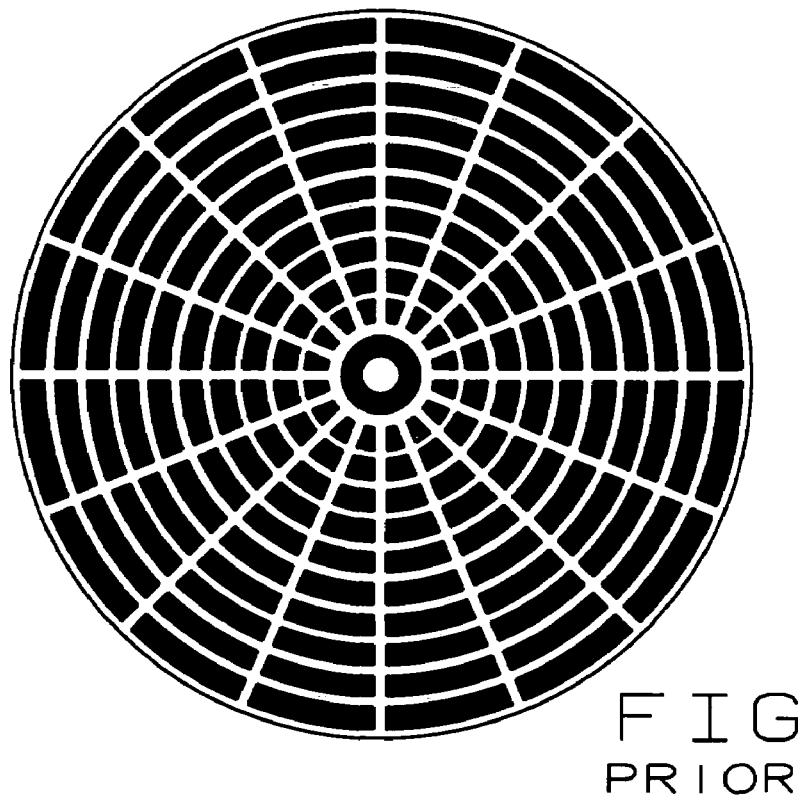
FIG. 2 is a depiction of a prior art spider-web like pattern.
Figure 3:
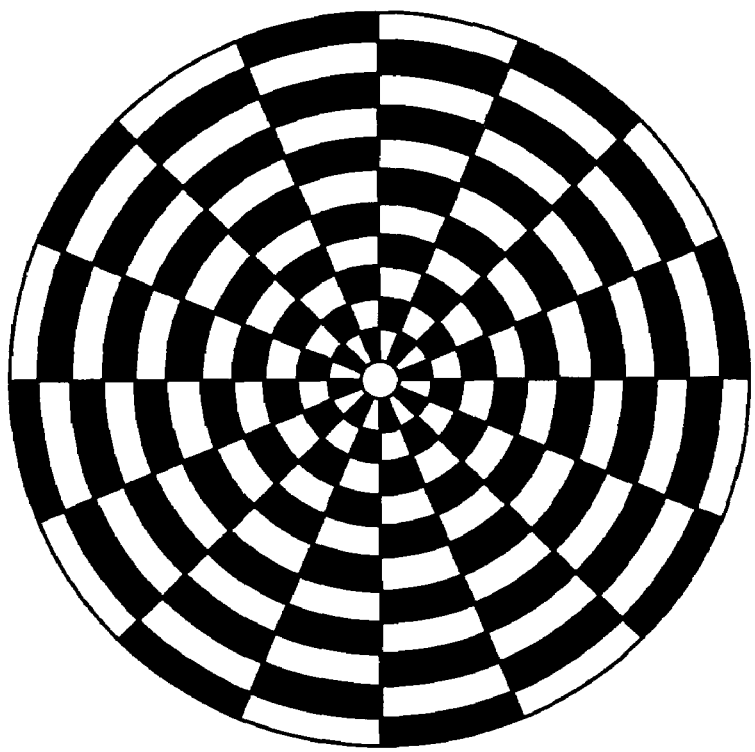
FIG. 3 is a prior art depiction of a dartboard placido pattern.

FIGS. 18–21 disclose how a placido pattern, in accordance with the present invention, can identify a concentric anomaly quite easily and simply without using complicated and difficult to implement algorithms with the use of patterns, such as those shown above in FIGS. 2 and 3. By the simple insertion of geometric shapes within the rings, concentric anomalies can be identified.

Figure 18:
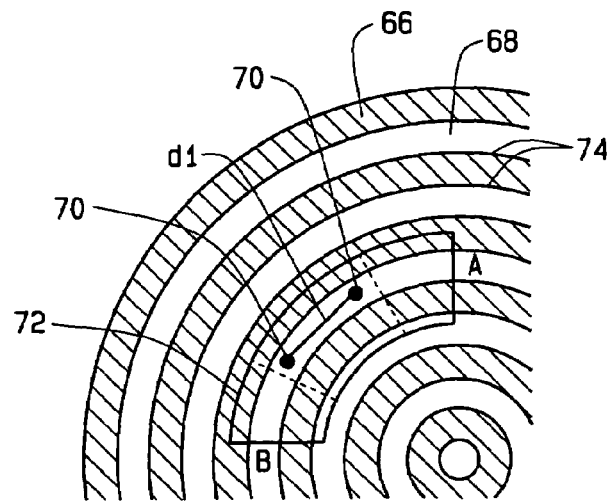
FIG. 18 is a partial view of a placido pattern in accordance with the present invention including a surface segment.
Figure 20:
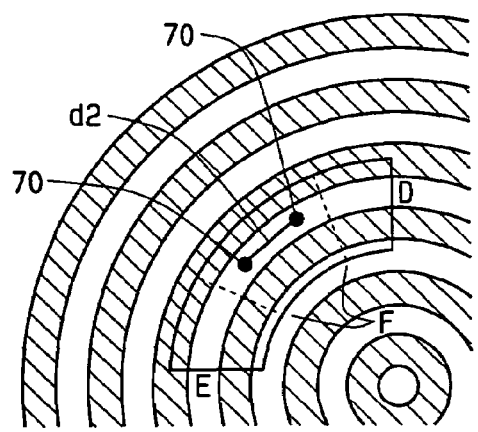
FIG. 20 is a partial view of a placido pattern in accordance with the present invention including a surface segment.

FIG. 18 shows a partial placido image having rings 66 and 68. For simplicity sake, only geometric shapes 70 within the surface segment 72 are shown. Though it is to be understood that other geometric shapes 70 are placed about the placido pattern within rings 66 and 68, as described above with respect to FIGS. 4–7.

Figure 19:
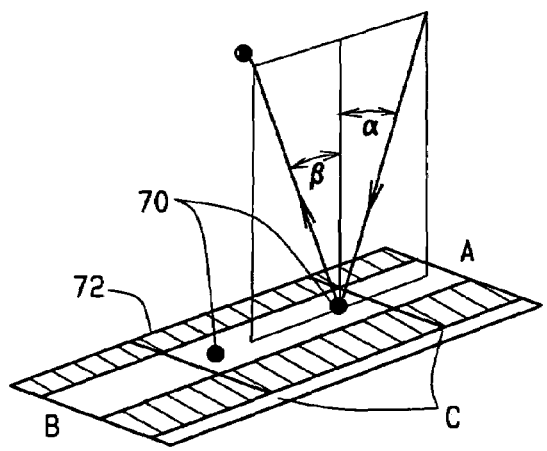
FIG. 19 depicts the surface segment of FIG. 18 including the reflected image.
Figure 21:
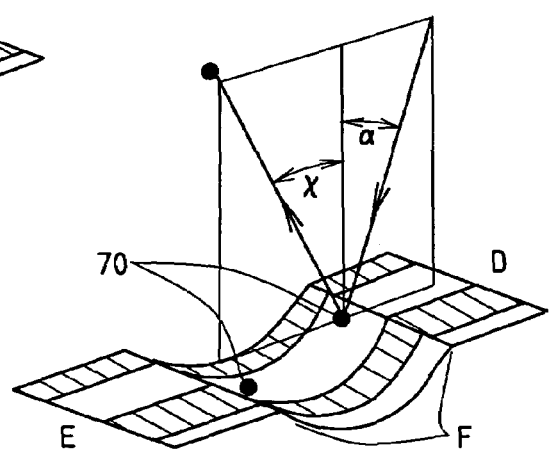
FIG. 21 depicts the surface segment of FIG. 20 including the detection of a concentric anomaly.

FIG. 19 shows surface segment 72 with shapes 70 wherein the angle alpha and beta are equal to each other when there is no anomaly. It is noted that everything in FIGS. 18–21 are identical of those of FIGS. 14–17 with the exception of the referenced geometric shapes 70 being added inside a ring. Again, edges 74 show little or no distortion with the anomaly of FIGS. 20 and 21. However because of the geometric shapes 70, the distortion causes the position of the marks to change. This change is shown as a difference between the distances D1 and D2 of FIGS. 18 and 20. Therefore, the addition of the circular dots 70 establishes a frame of reference where the concentric anomalies can be identified and better analyzed.

As those skilled in the art will understand the system described above, is very easily able to detect concentric curvature anomalies. In addition, the use of existing image processing algorithms with little or no modification can be used to detect those concentric anomalies. Instead of using complex edge detection algorithms needed for FIGS. 2 and 3, the present invention can detect a distortion in the series of geometric shapes in the radial pattern using known centroding algorithms. These centroding algorithms track the position changes of the dots by tracking the center of a dot covering multiple pixels in a stored image.

Thus, has been shown an inventive placido pattern that simply and effectively detects concentric anomalies more simply and straightforward then has been possible heretofore.

We claim:

1. An ophthalmic placido pattern for use in determining a curvature of an anterior surface of a cornea of an eye, the pattern comprising:
    a series of alternating light and dark concentric rings centered about a central point, wherein each concentric ring is continuous without any radial lines or edges;
    a series of spaced geometric shapes placed about and within at least some of the concentric rings, wherein the shapes are of a contrasting color with respect to the ring on which the shape is placed.

2. The placido pattern of claim 1, wherein the geometric shapes are circular dots.

3. The placido patter of claim 1, wherein the geometric shapes are light colored relative to the rings onto which they are placed.

4. The placido pattern of claim 1, wherein the geometric shapes are dark colored relative to the rings onto which they are placed.

5. The placido pattern of claim 1, wherein geometric shapes are placed on every ring.

* * * * *